(12) United States Patent
Horsmon et al.

(10) Patent No.: US 12,324,723 B1
(45) Date of Patent: Jun. 10, 2025

(54) NOSE-ONLY INHALATION EXPOSURE PLETHYSMOGRAPH FOR RABBITS

(71) Applicant: U.S. Army Combat Capabilities Development Command, Chemical Biological Center, Apg, MD (US)

(72) Inventors: Michael S Horsmon, Joppa, MD (US); Dennis B Miller, Rising Sun, MD (US)

(73) Assignee: U.S. Army as Represented by the Secretary of the Army, Washington, DC (US)

( * ) Notice: Subject to any disclaimer, the term of this patent is extended or adjusted under 35 U.S.C. 154(b) by 622 days.

(21) Appl. No.: 17/852,817

(22) Filed: Jun. 29, 2022

(51) Int. Cl.
*A61D 3/00* (2006.01)
*A01K 15/04* (2006.01)
*A61B 5/08* (2006.01)

(52) U.S. Cl.
CPC ............... *A61D 3/00* (2013.01); *A01K 15/04* (2013.01); *A61B 5/08* (2013.01); *A61B 2503/40* (2013.01); *A61D 2003/003* (2013.01)

(58) Field of Classification Search
CPC ..... A61D 3/00; A61D 2003/003; A01K 15/04
See application file for complete search history.

(56) References Cited

U.S. PATENT DOCUMENTS

| | | | | |
|---|---|---|---|---|
| 3,137,273 A * | 6/1964 | Greenwood | ......... | A01K 1/0613 119/754 |
| 3,368,530 A * | 2/1968 | Bearss | ................... | A01K 15/04 119/734 |
| 3,625,185 A * | 12/1971 | Kester | .................... | A01K 1/031 119/58 |
| 3,739,751 A * | 6/1973 | Mohr | ....................... | A61D 3/00 119/752 |
| 4,228,765 A * | 10/1980 | Berlin | ...................... | A61D 3/00 119/752 |
| 4,332,244 A * | 6/1982 | Levy | ....................... | A61D 7/04 128/206.28 |
| 4,660,572 A * | 4/1987 | Maruyama | ............... | A61N 5/04 219/693 |
| 4,841,982 A * | 6/1989 | Nikiforov | ............ | A01K 29/005 600/560 |
| 5,320,069 A * | 6/1994 | Anderson, Jr. | ...... | A01K 1/0613 119/757 |
| 6,651,587 B1 * | 11/2003 | DeFord | .................... | A61D 3/00 119/420 |

(Continued)

*Primary Examiner* — Michael H Wang
(74) *Attorney, Agent, or Firm* — Ulysses J. Biffoni; Timothy M. Barlow (57) ABSTRACT

A plethysmography apparatus for a rabbit includes a head portion, a neck restraint, and a body portion. The head portion includes a wall, a head cone configured to receive a head of a rabbit and accommodate nose-only inhalation, and a foot box configured to receive a front foot of the rabbit. The neck restraint includes a yoke defining an opening configured to receive and retain a neck of the rabbit and a seal configured to seal around the neck of the rabbit. A box extension can be inserted between the head portion and a body portion to more comfortably accommodate the ears of the rabbit. The body portion includes a housing formed of a side wall and an end wall that define a chamber configured to hold a body of the rabbit from neck to tail. The body portion is configured to sealably engage with the wall of the head portion at an end of the housing.

20 Claims, 6 Drawing Sheets

(56) References Cited

U.S. PATENT DOCUMENTS

| | | | | |
|---|---|---|---|---|
| 7,162,977 | B1* | 1/2007 | Charvat | A61D 3/00 |
| | | | | 472/75 |
| 8,028,663 | B2* | 10/2011 | Chen | A61D 3/00 |
| | | | | 119/815 |
| 8,590,487 | B1* | 11/2013 | Goddard, Jr. | A61B 6/527 |
| | | | | 119/751 |
| 8,628,479 | B2* | 1/2014 | Lomask | A61B 5/091 |
| | | | | 600/529 |
| 2004/0204642 | A1* | 10/2004 | Ferris | A61B 5/702 |
| | | | | 600/417 |
| 2005/0251053 | A1* | 11/2005 | Lomask | A61D 3/00 |
| | | | | 600/504 |
| 2008/0168948 | A1* | 7/2008 | Truitt | A61D 3/00 |
| | | | | 119/843 |
| 2010/0056899 | A1* | 3/2010 | Toddes | G01R 33/30 |
| | | | | 119/729 |
| 2011/0168107 | A1* | 7/2011 | Yaniv | A01K 1/0613 |
| | | | | 119/751 |
| 2012/0330130 | A1* | 12/2012 | Lanz | A61B 5/055 |
| | | | | 600/411 |
| 2017/0156296 | A1* | 6/2017 | Hayman, Jr. | A61B 5/702 |
| 2017/0354487 | A1* | 12/2017 | Klose | A61B 5/70 |

* cited by examiner

NOSE-ONLY INHALATION EXPOSURE PLETHYSMOGRAPH FOR RABBITS

GOVERNMENT INTEREST

The invention described herein may be manufactured, used, and/or licensed by or for the United States Government.

FIELD OF THE INVENTION

The present invention relates to the technical field of plethysmography, and in particular to a plethysmograph by which the respiratory parameters of a rabbit can be quantified and digitally recorded during nose-only inhalation experiments.

BACKGROUND OF THE INVENTION

The technique of plethysmography has been around for quite a long time and is often cited as the gold standard technique to quantify respiratory function by measuring changes in volume in different parts of a body. In research animal models, there are several ways to accomplish plethysmograph recordings. Each method has its own advantages and disadvantages. Only three techniques apply to inhalation toxicology studies involving animals. The first being whole-body plethysmography in which a chamber large enough to house the animal serves both as a plethysmograph and an exposure apparatus. Second, head-out plethysmography, in which the breathing zone (head) is separated from the body by a physical barrier and restraint of the animal. Third, nose-only plethysmography in which the nose of the animal is separated from the body by a physical barrier and restraint of the animal.

The goal of any plethysmograph design is to capture the expansion and contraction of the thorax of the animal. The expansion and contraction causes a change in pressure inside an enclosed chamber. The pressure is regulated by fine mesh screens placed over a small hole in the chamber surrounding the animal; thus allowing air to escape but at a regulated rate. A differential pressure transducer (DPT) is connected to the chamber and senses the changes in pressure while an analog to digital converter digitizes that data for analysis by a computer software system. The signal from the DPT is calibrated to known airflow values. From this calibrated pressure one can very accurately measure the change in airflow associated with expansion of the animals' thorax when it inhales. The volume is then derived from the flow rate over time. The volume of air displaced in the chamber by inhalation is the same as the volume of air inhaled by the animal. From this relationship one can derive the tidal volume and a host of other parameters that describe the respiratory function of an animal.

With most small research animal models any of the three approaches above will work. The best technique is either head out (for measuring the effect of a substance on respiration when dosing through any route other than inhalation) or nose-only (for measuring the effects of a substance on respiration when dosed by inhalation). Whole-body plethysmography is less desirable as it is complicated by having a dynamic flow, movement artifact from the animal, and subject to changes in humidity which can affect the measured flow. However, as of now the only commercially available apparatus for inhalation dosing studies with rabbits is the whole-body plethysmograph. Furthermore, while there are head-out plethysmograph designs available that will fit some rabbits, these are not functional for nose-only type of exposures (a more common type of exposure). This is because there are specific issues with creating a nose-only plethysmograph for rabbits that are related to the unique anatomy of a rabbit.

Thus, there is a need for a plethysmography apparatus that functions as both a head-out plethysmograph as well as a nose-only exposure restraint that is uniquely designed to work with the specific anatomy of a rabbit to provide a means by which the respiratory parameters of a rabbit can be quantified and digitally recorded during nose-only inhalation experiments.

SUMMARY OF THE INVENTION

The present invention provides a plethysmography apparatus for rabbits. Embodiments of the inventive plethysmography apparatus functions as both a head-out plethysmograph as well as a nose-only exposure restraint that is uniquely designed to work with the specific anatomy of a rabbit to provide a means by which the respiratory parameters of a rabbit can be quantified and digitally recorded during nose-only inhalation experiments. The plethysmography apparatus includes a head portion, a neck restraint, and a body portion. The head portion includes a wall, a head cone, and foot box extending from the wall. The head cone is configured to receive a head of a rabbit via a head opening defined in the wall and the foot box is configured to receive at least one front foot of the rabbit via a foot opening defined in the wall. The neck restraint includes a yoke defining an opening configured to receive and retain a neck of the rabbit and a seal configured to seal around the neck of the rabbit. The neck restraint is configured to be coupled and sealed to the wall of the head portion. The body portion includes a housing formed of at least one side wall and an end wall that define a chamber that is configured to hold a body of the rabbit from neck to tail.

BRIEF DESCRIPTION OF THE DRAWINGS

The present invention is further detailed with respect to the following figures that depict various aspects of the present invention.

DETAILED DESCRIPTION OF THE PREFERRED EMBODIMENTS

The present invention has utility as a plethysmography apparatus that functions as both a head-out plethysmograph as well as a nose-only exposure restraint that is uniquely designed to work with the specific anatomy of a rabbit to provide a means by which the respiratory parameters of a rabbit can be quantified and digitally recorded during nose-only inhalation experiments.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below. As used in the description of the invention and the appended claims, the singular forms "a," "an" and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

Figure 5:
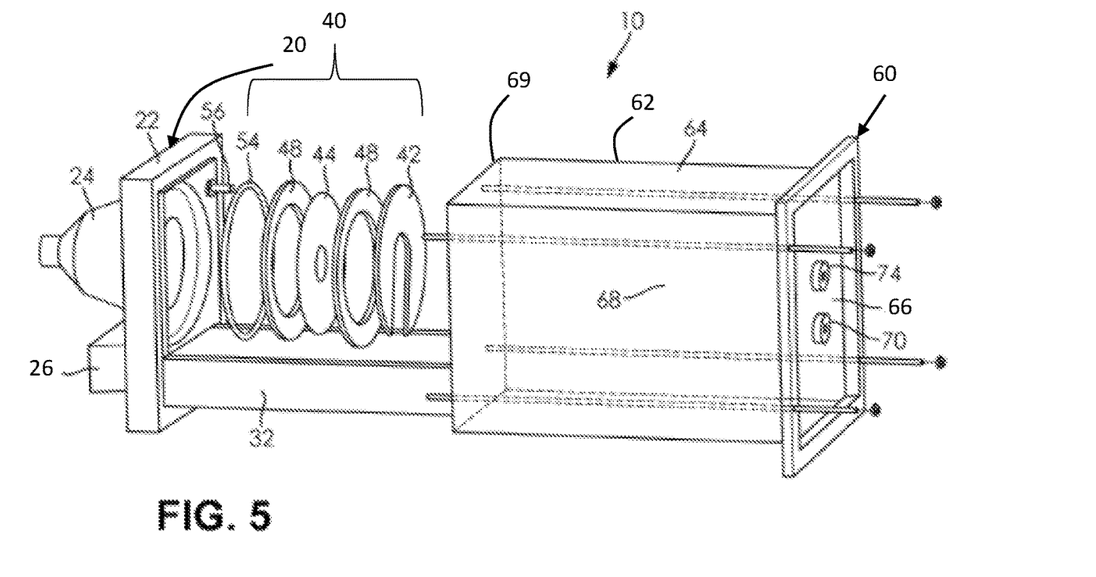
FIG. 5 is an exploded perspective view of a plethysmography apparatus for rabbits according to embodiments of the present invention.

Referring now to the drawings, as shown in FIG. 5 a plethysmography apparatus 10 for rabbits according to embodiments of the present invention includes a head portion 20, a neck restraint 40, and a body portion 60. The components of the inventive plethysmography apparatus 10 for rabbits may be formed of any suitable non-porous material that is capable of holding the required pressure associated with such devices.

Figure 3:
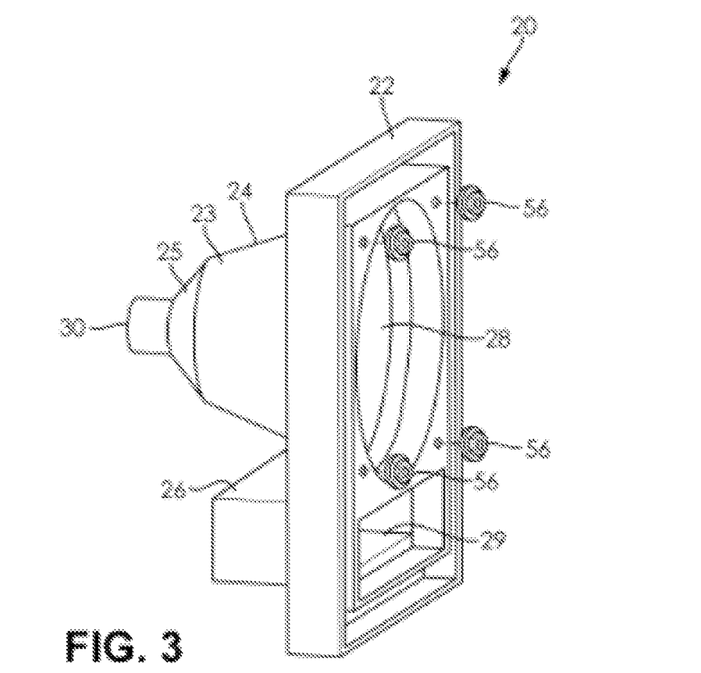
FIG. 3 is a perspective view of a head portion of a plethysmography apparatus for rabbits according to embodiments of the present invention.

As shown in FIG. 3, the head portion 20 includes a wall 22, a head cone 24 that extends from the wall 22, and a foot box 26 that also extends from the wall 22. According to embodiments, the wall is generally planar, as shown. The head cone 24 has a tapered shape with a first portion 23 that is tapered at a first angle and a second portion 25 that is tapered at a second angle. According to embodiments the second angle is greater than the first angle, meaning that the wall of the head cone 24 that forms the second portion 25 has a steeper taper than the wall of the head cone 24 that forms the first portion 23. The head come 24 is configured to receive a head of a rabbit via a head opening 28 defined in the wall 22. Specifically, the first portion 23 of the head cone 24 is configured to retain the head and ears of a rabbit, while the second portion 25 is configured to retain the nose of the rabbit. The tapered configuration of the head cone 24 with the first tapered portion 23 and the second steeper tapered portion 25 urges the nose of the rabbit into the narrower second portion 25 with the nose of the rabbit positioned near an inlet opening 30 of the head cone 24, which is opposite the head opening 28. The inlet opening 30 is configured to attach to a traditional nose-only exposure chamber port (not shown) used in toxicity testing. The foot box 26, which is positioned below the head cone 24 and extends from the wall 22 in the same direction as the head cone 24, is configured to receive at least one front foot of the rabbit via a foot opening 29 defined in the wall 22. According to embodiments, the foot box 26 is sealed to the wall 22 of the head portion 20. According to embodiments, the foot box 26 is configured to be an air tight chamber when sealed with other components of the plethysmography apparatus 10. According to embodiments, the foot box 26 is rectangular, as shown in FIG. 3, however, other geometries suitable for receiving the foot or feet of a rabbit are also contemplated. Accordingly, the foot box 26 is isolated from the breathing zone, as described below, while allowing the rabbit to maintain a normal body posture.

Figure 4:
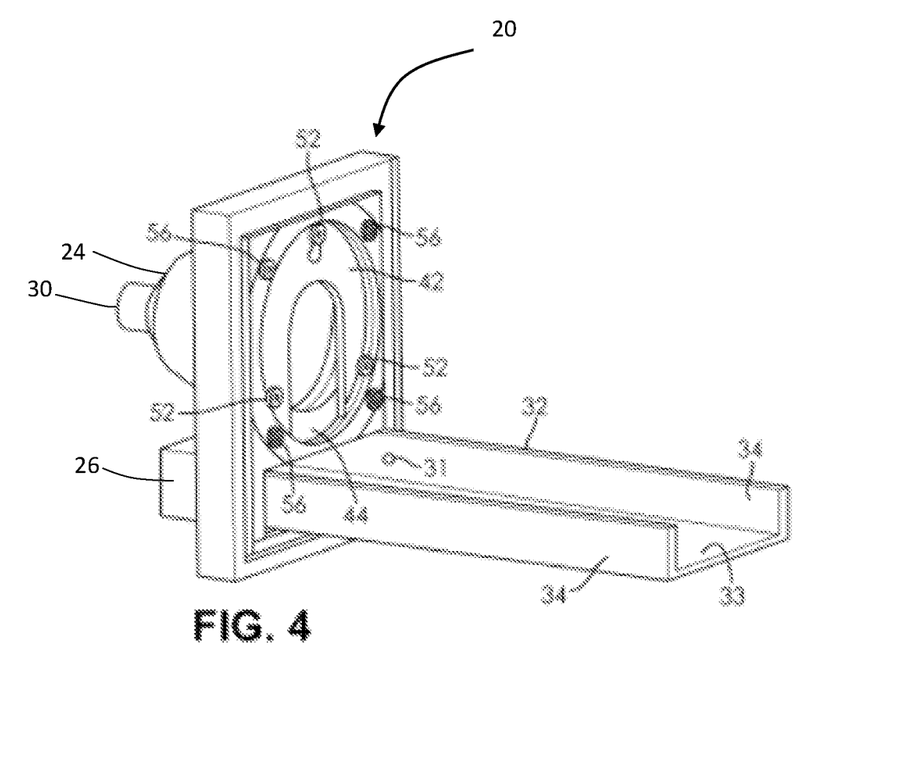
FIG. 4 is a perspective view of the neck portion of FIG. 2 installed within the head portion of FIG. 3 according to embodiments of the present invention.

According to embodiments, the head portion 20 of an inventive plethysmography apparatus 10 additionally includes a positioning tray 32 that extends from the wall 22 of the head portion 20 in a direction away from the foot box 26. As shown in FIG. 4, the positioning tray 32 is positioned under the foot opening 29 in the wall of the head portion 20. This relationship of the positioning tray 32 and the foot box 26 allows the rabbits feet to be positioned within the foot box 26 while the rabbit's body is supported by the positioning tray 32. The positioning tray 32 is configured to be coupled to the head portion 20 within the foot opening 29 defined in the head portion 20, for example using fasteners 31. As shown in FIG. 4, according to embodiments, the positioning tray 32 includes a bottom wall 33 that is configured to support the body of a rabbit and may additionally include side walls 34 that extend from the bottom wall 33. As shown in FIG. 4, the side walls 34 have a relatively short height compared to the wall 22 of the head portion 20, for example. The positioning tray 32 may be used to support the body of a rabbit as the rabbit's head is positioned within the head portion 20 of the plethysmography apparatus 10 to aid in getting the rabbit's body into the body portion 60 of the plethysmography apparatus 10 for experimentation.

Figure 2:
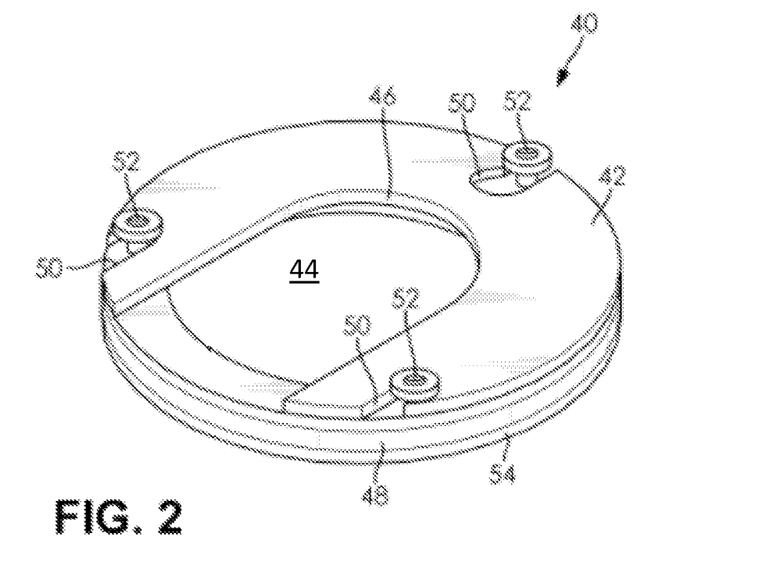
FIG. 2 is a perspective view of a first embodiment of a neck restraint of a plethysmography apparatus for rabbits according to embodiments of the present invention.

The neck restraint 40, as shown in FIG. 2, includes a yoke 42 and a seal 44. The yoke 42 defines an opening 46 that is configured to receive and retain a neck of the rabbit. As shown, the opening 46 is U-shaped. This shape allows the yoke 42 to fit around the rabbit's neck and prevents the head from slipping backward through the yoke 42 and away from the head portion 20. The seal 44 is configured to seal around the neck of the rabbit. According to embodiments, the seal 44 is formed of latex or other elastomer material that illustratively include neoprene and silicone. According to some inventive embodiments, the seal 44 is sandwiched between the rings 48 and 54 of the neck restraint 40, which according to some inventive embodiments, includes a ring 48 to which the yoke 42 and the seal 44 are coupled. Such a ring 48 provides structural rigidity of the neck restraint 40. In use, once a rabbit's neck is positioned within the yoke 42, and the neck restraint 40 it is configured to be coupled to the wall 22 of the head portion 20 using a plurality of fasteners 56, as shown in FIG. 4. According to embodiments, the neck restraint 40 is configured to be installed in the head opening 28 defined in the wall 22 of the head portion 20. According to embodiments, the neck restraint 40 additionally includes an sealing ring 54 configured to seal the neck restraint 40 to the wall of the head portion 20 when the neck restraint 40 is installed in the head opening 28 defined in the wall 22 of the head portion 20. According to embodiments, the yoke 42 is interchangeable within the neck restraint 40 to provide openings 46 of different sizes in order to accommodate rabbits of various sizes. To provide further adjustability, according to embodiments, the yoke 42 defines a plurality of adjustment channels 50 in which a plurality of yoke locking pins 52 are adjustably disposed to allow the yoke 42 to be moved to various positions relative to the rest of the neck restraint 40, thereby adjusting the size of the opening 46 therein. As shown in FIG. 5, the neck restraint 40

Figure 1:
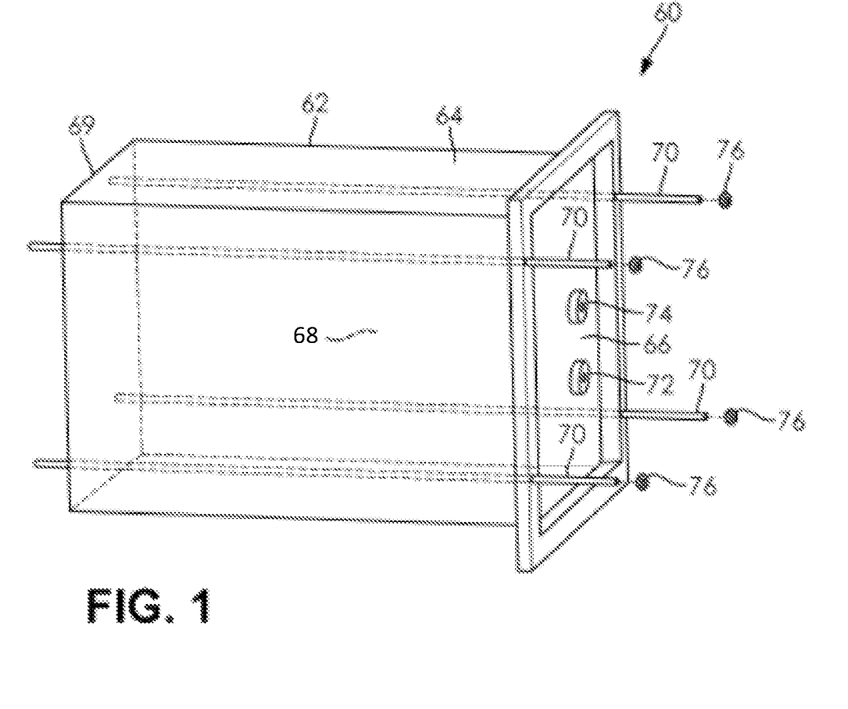
FIG. 1 is a perspective view of a body portion of a plethysmography apparatus for rabbits according to embodiments of the present invention.

The body portion 60 of an inventive plethysmography apparatus 10 includes a housing 62 formed of at least one side 64 wall and an end wall 66. The side wall 62 may be formed in a circular or tube shape, a triangular shape, or a rectangular shape, as shown in FIG. 1. When the housing 62 is rectangular as shown, the side wall 64 may be considered to include four side wall 64. The housing 62 defines a chamber 68 that is configured to surround a body of the rabbit from neck to tail. The body portion 60 is configured to engage with the wall 22 of the head portion 20 at an end 69 of the housing 60 that is opposite the end wall 66 of the housing 60. As shown in FIG. 5, the end 69 of the housing 60 engages the wall 22 of the head portion 20 on a side of the head portion 20 that is opposite to the head cone 24 and foot box 26. When the housing 62 is engaged with the wall 22 of the head portion 20, the housing 62 encircles the foot opening 29 and the head opening 28 of the head portion 20. Accordingly, the body chamber 68 is then in fluid communication with the head cone 24 via the head opening 28 and in fluid communication with the foot box 26 via the foot opening 29. However, when a rabbit is positioned within the neck restrain 40 and the neck restraint 40 is positioned within the head opening 28 of the head portion, the seal 44 around the rabbit's neck along with the rabbit's neck itself block the fluid communication between the body chamber 68 and the space within the head cone 24; however, the space within the foot box 26 is still in sealed fluid communication with the body chamber 68 even when the rabbits feet are positioned in the space within the foot box 26. According to embodiments, the body portion 60 includes a plurality of threaded rods 70 for attaching the housing 62 to the head portion 20 using a plurality of associated fasteners 76. According to embodiments, the body portion 60 includes a port 72 configured for a pneumotachograph screen. As shown in FIG. 1, the port 72 for the pneumotachograph screen is provided in the end wall 66 but may alternatively be provided in the side wall 64. The pneumotachograph screen provides resistance to airflow and allows for pressure to build when the animal breathes. This pressure is measured through the use of a differential pressure transducer (DPT), which, according to embodiments, is placed in the second port 74 of the body portion 60. As shown in FIG. 1, the port 74 for the differential pressure transducer is provided in the end wall 66 but may alternatively be provided in the side wall 64. The DPT may be designed such that the positive side will be connected to the port 74 on the body chamber and the negative side either open to the surrounding atmosphere or connected to a port on a reference chamber attached to the back of the body tube. The analog signal from the DPT is converted to digital data and is calibrated to known airflow rates before use. From this calibrated signal, a host of respiratory parameters are either directly measured or derived.

Figure 6:
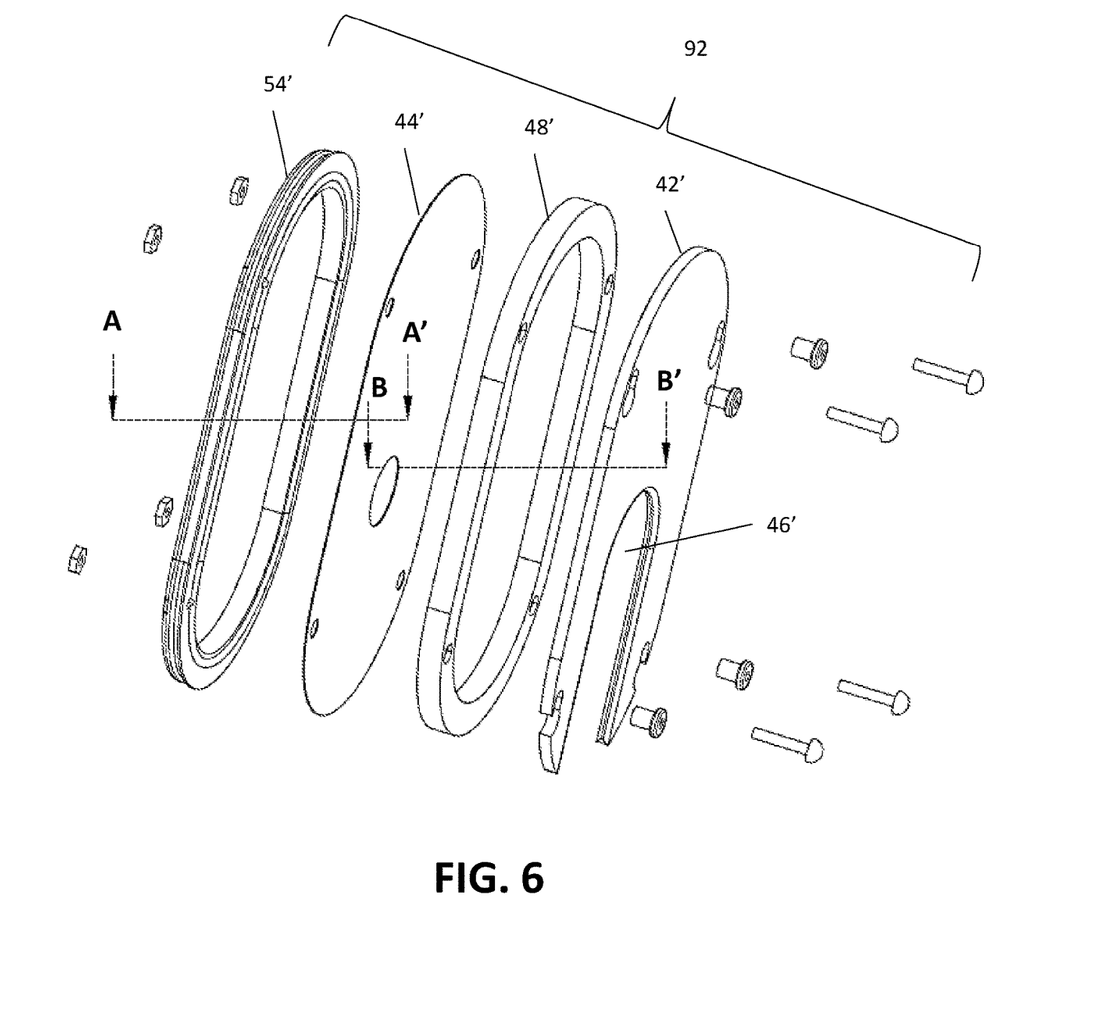
FIG. 6 is an exploded perspective view of another embodiment of a neck restraint of a plethysmography apparatus for rabbits according to embodiments of the present invention.
Figure 7A:
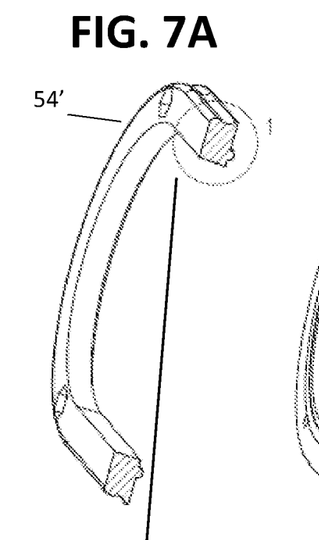
FIG. 7A is a cross-sectional view along line A-A' through the ring of FIG. 6.
Figure 7B:
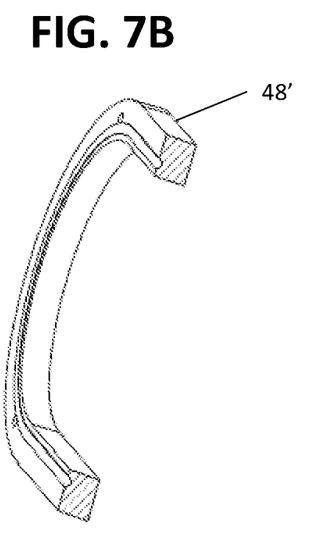
FIG. 7B is a cross-sectional view along line B-B' through the seal show in FIG. 6.
Figure 7C:
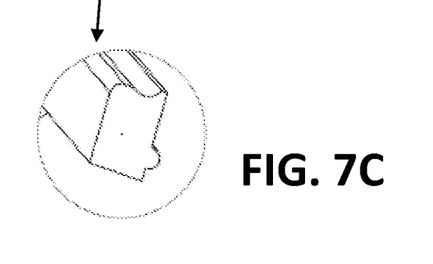
FIG. 7C is a magnified view of the cross section of FIG. 7A.
Figure 8:
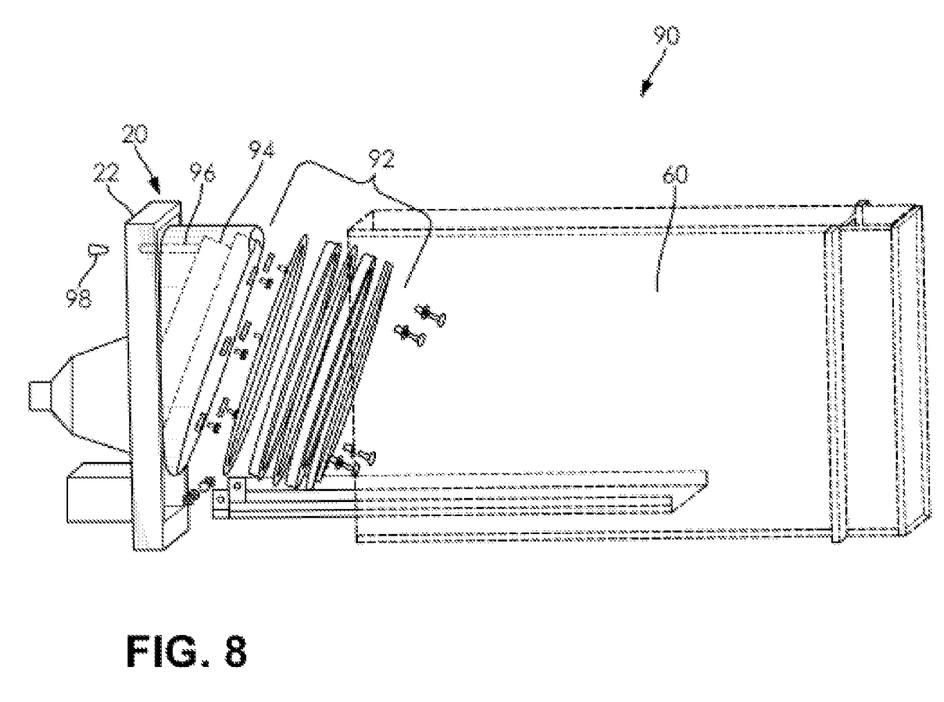
FIG. 8 is an exploded perspective view of another plethysmography apparatus for rabbits according to embodiments of the present invention.

Referring now to FIGS. 6-8 in which like reference numerals correspond to the meanings ascribed thereto above, a plethysmography apparatus 90 for rabbits according to another embodiment of the present invention includes a head portion 20, a neck restraint 92, and a body portion 60. The components of the inventive plethysmography apparatus 90 for rabbits may be formed of any suitable non-porous material that is capable of holding the required pressure associated with such devices. The plethysmography apparatus 90 affords certain ergonomic attributes to achieve a more comfortable placement of a rabbit therein relative to apparatus 10, as well as providing a superior seal about the rabbit thereby resulting in more accurate data collection As shown in FIG. 8, the head portion 20 with like components detailed with respect to FIGS. 3-5 includes a box extension 94 to house the rabbit's ears. In some inventive embodiments, the box extension is tilted with respect to a sample port 96 that also engages the wall 22 and a sample port plug 98. It is appreciated that an ear within the box extension 94 is accessed via sample port 96 for data or sample collection. By way of example, pulsometry, blood draw collection, blood gas sensing, or combination thereof. The box extension adapted to house the ears of a rabbit whose head is within the head cone 24 such that the ears rest in a more natural position The neck restraint 92, as shown in FIGS. 6 and 8 is ellipse-shaped to more comfortably accommodate a rabbit and includes an ellipse-shaped-yoke 42' and a complementary seal 44'. The yoke 42' defines an opening 46' that is configured to receive and retain a neck of the rabbit. As shown, the opening 46' is U-shaped. This shape allows the yoke 42' to fit around the rabbit's neck and prevents the head from slipping backward through the yoke 42' and away from the head portion 20, the ears extending in a nature position diagonally upward from the head of the rabbit. The seal 44' is configured to seal around the neck of the rabbit. According to embodiments, the seal 44' is formed of latex or other biocompatible elastomeric material. According to some inventive embodiments, the seal 44' is sandwiched between the rings 48' and 54' of the neck restraint 40', which according to some inventive embodiments, includes a ring 48 to which the yoke 42 and the seal 44 are coupled, which according to some inventive embodiments, includes a ring 48' to which the yoke 42' and the seal 44' are coupled. Such a ring 48' provides structural rigidity of the neck restraint 92. A cross-sectional view of the ring 48' is shown in FIG. 7B that shows a rectilinear cross-section thereto. It is appreciated that other cross sectional shapes are operative herein. These cross sectional shapes for ring 48' illustratively include circular, ellipse, triangular, and polygonal shapes with 5 to 12 sides. In use, once a rabbit's neck is positioned within the yoke 42', the neck restraint 92 is configured to be coupled to the box extension 94 using a plurality of fasteners 56, as shown in FIG. 8. According to embodiments, the neck restraint 92 is configured to be installed in the box extension 94 that is coupled with head opening 28 defined in the wall 22 of the head portion 20. According to some inventive embodiments, the neck restraint 92 additionally includes a sealing ring 54' configured to seal the neck restraint 92 to the box extension 94 when the neck restraint 92 is coupled thereto. A cross-sectional view of the sealing ring 54' is shown in FIG. 7A that shows a complex curved cross section. A magnified view of this cross sectional upper edge is shown in FIG. 7C. It is appreciated that other cross sectional shapes are operative herein that illustratively include circular, ellipse, triangular, and polygonal shapes with 5 to 12 sides. According to embodiments, the yoke 42' is interchangeable within the neck restraint 92 to provide openings 46' of different sizes in order to accommodate rabbits of various sizes. To provide further adjustability, according to embodiments, the yoke 42' defines a plurality of adjustment channels 50' in which a plurality of yoke locking pins 52 are adjustably disposed to allow the yoke 42' to be moved to various positions relative to the rest of the neck restraint 92, thereby adjusting the size of the opening 46 therein.

The overall design of inventive plethysmography apparatus 10 or 90 allows it to function as a true head out plethysmograph that can be attached to and used as a restraint for nose-only inhalation exposures of rabbits.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A plethysmography apparatus for a rabbit, comprising:
   a head portion comprising a wall, a head cone extending from the wall, and a foot box extending from the wall, the head cone configured to receive a head of the rabbit via a head opening defined in the wall and the foot box configured to receive at least one front foot of the rabbit via a foot opening defined in the wall;
   a neck restraint comprising a yoke and a seal, the yoke defining an opening configured to receive and retain a neck of the rabbit, the seal configured to seal around the neck of the rabbit; and
   a body portion comprising a housing formed of at least one side wall and an end wall, the housing defining a chamber configured to hold a body of the rabbit, the body portion configured to engage with the wall of the head portion at an end of the housing that is opposite the end wall of the housing.

2. The plethysmography apparatus of claim 1, wherein the head cone has a first tapered portion that is tapered at a first angle and a second tapered portion that is tapered at a second angle that is steeper than the first angle, so that the first tapered portion is configured to retain the head and ears of the rabbit and the second tapered portion is configured to retain the nose of the rabbit, and the head cone defines an inlet opening adjacent to the second tapered portion and opposite the head opening.

3. The plethysmography apparatus of claim 1, wherein the foot box is sealed to the wall of the head portion.

4. The plethysmography apparatus of claim 1, wherein the foot box is an airtight part of the body chamber.

5. The plethysmography apparatus of claim 1, further comprising a box extension intermediate between the head portion and the neck restraint, the box extension sized to accommodate ears of the rabbit.

6. The plethysmography apparatus of claim 5, wherein the box extension is tiltable relative to the head portion.

7. The plethysmography apparatus of claim 1, wherein the foot box is positioned under the head cone.

8. The plethysmography apparatus of claim 1, wherein the head portion further comprises a positioning tray that extends from the wall of the head portion in a direction away from the foot box.

9. The plethysmography apparatus of claim 8, wherein the positioning tray is positioned under the foot opening in the wall of the head portion.

10. The plethysmography apparatus of claim 8, wherein the positioning tray is configured to be coupled to the head portion within the foot opening defined in the head portion.

11. The plethysmography apparatus of claim 1, wherein the neck restraint further comprises a ring to which the yoke and the seal are coupled, the neck restraint having a shape that is an ellipse or a circle.

12. The plethysmography apparatus of claim 1, wherein the yoke defines a plurality of adjustment channels in which a plurality of yoke locking pins are adjustably disposed.

13. The plethysmography apparatus of claim 1, wherein the seal is formed of an elastomeric material.

14. The plethysmography apparatus of claim 1, wherein the neck restraint further comprises a sealing ring configured to seal the neck restraint to the wall of the head portion.

15. The plethysmography apparatus of claim 1, wherein the neck restraint is configured to be coupled to the wall of the head portion using a plurality of fasteners.

16. The plethysmography apparatus of claim 1, wherein the neck restraint is configured to be installed in the head opening defined in the wall of the head portion.

17. The plethysmography apparatus of claim 1, wherein the housing is configured to receive a positioning tray of the head portion.

18. The plethysmography apparatus of claim 1, wherein the housing encircles the foot opening and the head opening of the head portion.

19. The plethysmography apparatus of claim 1, wherein the body portion further comprises a plurality of threaded rods for attaching the housing to the head portion.

20. The plethysmography apparatus of claim 1, wherein the body portion includes a port configured for a pneumotachograph screen or a differential pressure transducer.

* * * * *